US007245726B2

(12) United States Patent
Du et al.

(10) Patent No.: US 7,245,726 B2
(45) Date of Patent: Jul. 17, 2007

(54) NOISE CANCELING MICROPHONE SYSTEM AND METHOD FOR DESIGNING THE SAME

(75) Inventors: Yu Du, Blacksburg, VA (US); Michael A. Vaudrey, Blacksburg, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 523 days.

(21) Appl. No.: 10/928,895

(22) Filed: Aug. 27, 2004

(65) Prior Publication Data

US 2005/0031136 A1 Feb. 10, 2005

Related U.S. Application Data

(63) Continuation-in-part of application No. 09/970,356, filed on Oct. 3, 2001, now Pat. No. 6,963,649.

(51) Int. Cl.
*A61F 11/06* (2006.01)
*H04R 3/00* (2006.01)
*H04R 9/08* (2006.01)
*H04R 25/00* (2006.01)
*H04B 15/00* (2006.01)

(52) U.S. Cl. ....................... 381/71.7; 381/92; 381/356; 381/355; 381/369; 381/357; 381/358; 381/313; 381/71.1; 381/94.7; 379/433.03

(58) Field of Classification Search ............... 381/71.7, 381/186, 357, 355, 356, 358, 369, 313, 92, 381/122, 91, 71.1, 94.7; 379/433.03
See application file for complete search history.

(56) References Cited

U.S. PATENT DOCUMENTS 2,611,035 A * 9/1952 Duncan ..................... 381/94.9
3,995,124 A * 11/1976 Gabr .......................... 381/357
4,258,235 A * 3/1981 Watson ....................... 381/174

(Continued)

*Primary Examiner*—Vivian Chin
*Assistant Examiner*—Devona E. Faulk
(74) *Attorney, Agent, or Firm*—Roberts, Mardula & Wertheim, LLC

(57) ABSTRACT

A microphone housing improves the broadband noise canceling performance of an active noise canceling microphone system while also ensuring improved speech transmission through the system. First and second microphone elements are selected each having a diameter “d” and a thickness “t”. The two microphone elements are aligned axially with the back surfaces in contact and secured in an axially aligned cylindrical cavity within a cylindrically shaped housing. The cylindrically shaped housing has an outside diameter “D,” an interior cavity of diameter of “d,” and a height “2t”. The housing is exposed to an environment comprising both speech and noise. The first microphone element is adapted to receive a signal having both voice and noise components, while the second microphone element is adapted to receive a signal that is predominantly noise. A controller processes signals from the first microphone element and the second microphone element. The values of D and d are selected so to obtain a ratio of D over d between 1 and about 2.4 or a near field power difference of the first microphone signal and the second microphone signal between 8 dB and 11 dB. In the event the near field power difference is more than 11 dB, the outside diameter of the microphone housing “D” is reduced. In the event the near field power difference is less than 8 dB, the outside diameter of the microphone housing “D” is increased.

54 Claims, 13 Drawing Sheets

U.S. PATENT DOCUMENTS 5,303,307 A 4/1994 Elko et al.
5,319,736 A 6/1994 Hunt
5,329,593 A 7/1994 Lazzeroni et al.
5,442,713 A 8/1995 Patel et al.
5,473,684 A * 12/1995 Bartlett et al. .............. 379/395
5,473,702 A 12/1995 Yoshida et al.
5,511,130 A 4/1996 Bartlett et al.
5,600,729 A * 2/1997 Darlington et al. ........ 381/71.6
5,673,325 A * 9/1997 Andrea et al. ................ 381/92
5,854,848 A * 12/1998 Tate et al. .................. 381/357
5,917,921 A * 6/1999 Sasaki et al. .............. 381/94.1
5,953,380 A * 9/1999 Ikeda ......................... 375/346
5,978,824 A * 11/1999 Ikeda ......................... 708/322
6,009,184 A * 12/1999 Tate et al. .................. 381/357
6,614,911 B1 * 9/2003 Watson et al. ................ 381/86
6,665,410 B1 12/2003 Parkins

* cited by examiner

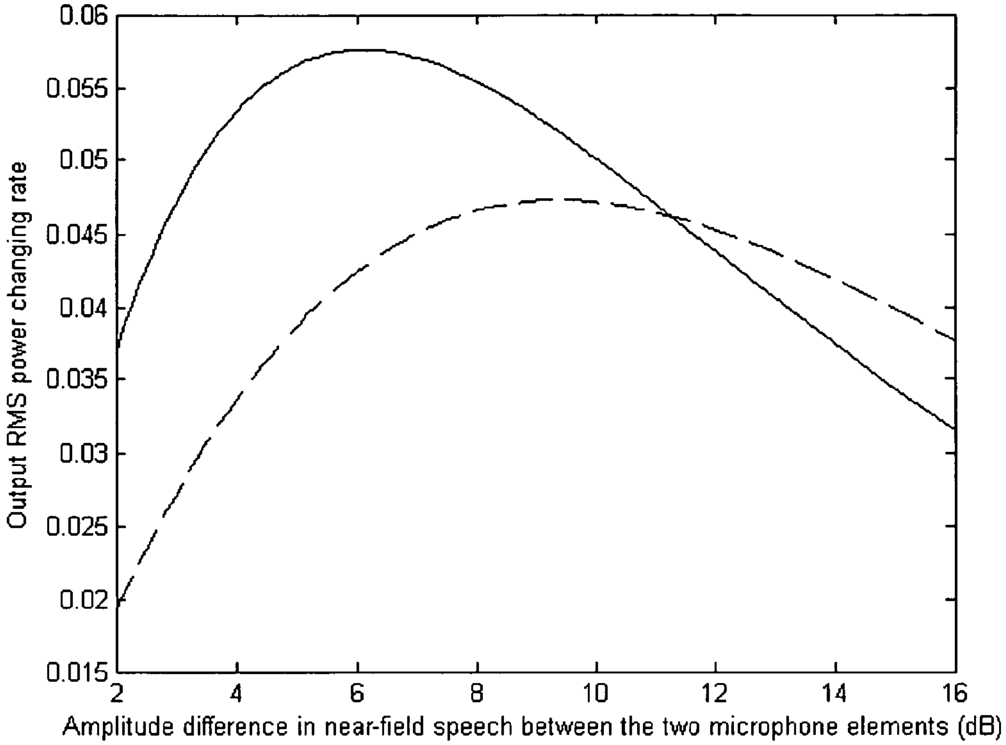
FIGURE 3B - Theoretical (solid) and Practical (dotted) rates of change of output power as a function of amplitude power difference in near and far microphones

NOISE CANCELING MICROPHONE SYSTEM AND METHOD FOR DESIGNING THE SAME

CROSS REFERENCE TO RELATED APPLICATIONS

This application is a continuation in part of application Ser. No. 09/970,356, filed Oct. 3, 2001, now U.S. Pat. No. 6,963,649 (the "Ser. No. 09/970,356 Application"). The Ser. No. 09/970,356 Application is incorporated herein by reference in its entirety for all purposes.

BACKGROUND

The present invention pertains generally to active noise canceling microphones and related devices. More particularly, the present invention relates to a method for designing an acoustically motivated housing and architecture for an active noise canceling microphone comprising two microphone elements, an analog or digital or hybrid (analog and digital) control circuitry and associated control codes or software. The new acoustic housing design method provides improved background noise canceling and enhanced speech intelligibility for such an active noise canceling microphone system as described herein. The performance improvement is realized due to the optimal acoustic design of the shape and dimensions of the microphone housing and the unique assembly method of the microphone elements inside the housing.

Noise canceling microphones are widely used in commercial, industry, and military applications where clear communication in noisy ambient environments is required. There are basically two types of noise canceling microphone designs. A passive noise canceling microphone typically incorporates a single membrane to sense ambient sound, where the housing of that membrane is open to the environment on both sides. Far-field sounds impact the membrane essentially equally on both sides, generating little net movement (particularly at low frequencies), and thus a low sensitivity. Near-field sounds (such as speech when the microphone is placed close to a speaker's mouth) cause the membrane to move significantly in one direction over another, thus causing a higher near-field sensitivity. This higher sensitivity to close-range voice versus lower sensitivity to far-field ambient noise provides a low frequency improvement in the signal-to-noise ratio because of the associated far-field noise rejection, thus improving low frequency speech intelligibility.

The case, or housing design, for passive noise canceling microphones usually concerns housing a single microphone element and providing for the ventilation of both sides of the membranes is discussed in U.S. Pat. Nos. 5,442,713, 5,854,848 and 6,009,184. The invention described herein is different from this prior art since it is related to a unique housing design for active noise canceling microphones using two omni-directional microphone elements.

U.S. Pat. No. 5,854,848 and U.S. Pat. No. 6,009,184, issued to Tate et. al. describe a noise control device for a boom mounted passive noise canceling microphone. This device utilizes a curved reflector attaching at the back surface of the microphone housing facing away from the desired signal source, or speaker's mouth. This prior art is shown to be effective for passive noise canceling microphones that reduce low frequency noise much more effectively than high frequency noise. It does not necessarily work for active noise canceling microphones since the effectiveness of the active element will be highly dependent on the broadband coherence between the two individual microphone elements. The addition of such a reflector on one side of the microphone housing as described by Tate will inevitably degrade the coherence between the two microphone elements especially at high frequencies. This may instead result in a degradation of the performance of the active noise canceling microphone.

Active noise canceling microphones typically utilize two individual microphone elements (preferably omni-directional electret microphones) and an active element such as a subtraction circuit is employed in order to electronically difference the two microphone signals. The two microphone elements are disposed such that a first microphone element receives the desired speech input and the background noise present in the vicinity of the speech, and a second microphone element senses substantially only the background noise. Therefore, a noise reduced speech signal can be generated when subtracting the second microphone signal from the first microphone signal by the active element of the active noise canceling microphone. The noise canceling performance of such an active noise canceling microphone is highly dependant on the broad band coherence between the two microphone elements. In addition, the level of the speech signal in the final output of such an active noise canceling microphone is directly related to the amplitude difference of the speech signals sensed by the two microphone elements.

U.S. Pat. No. 5,917,921 issued to Sasaki et. al., discusses the use of two microphone elements to form an active noise reducing microphone apparatus having an adaptive noise canceller. The Sasaki patent teaches that the two microphone units should be disposed in proximate locations, being oriented in the same direction or alternatively in opposite directions under certain circumstances. However, the Sasaki patent does not disclose or teach the effects of the microphone shape and dimensions on the coherence function and the amplitude difference in the desired signal sensed by the two microphone elements. These effects are very important in terms of the noise canceling performance and speech intelligibility achievable by the active noise canceling microphone apparatus. Secondly, the active noise canceling apparatus with two microphone elements facing the same or opposite directions taught in the Sasaki patent reduces primarily the low frequency wind noise. In an attempt to reduce the broadband background noise, much more strict constraints are required on the distance between the two microphone elements and the design of the acoustic baffle separating the two elements. And furthermore, the configuration of orienting the two microphone elements in the same direction is not a practical choice since such a configuration may result in a more effective speech canceller than a noise canceller.

U.S. Pat. No. 5,673,325 issued to Andrea describes an active noise canceling microphone for use with a telephone handset or a boom microphone device. This active noise canceling microphone again consists of two individual microphone elements arranged such that one microphone receives both the desired speech input and the background noise while the other microphone receives substantially only the background noise. The Andrea patent teaches that a small distance (preferably 0) between the two microphone elements is required to obtain good noise canceling performance. On the other hand, in order to prevent the active circuit from canceling the desired speech signal, an acoustic baffle is needed between the two microphone elements. However, the Andrea patent does not teach a specific size or shape of the acoustic baffle design so that both good noise canceling performance for background noise and a significant differentiation in near-field speech (desired signal) amplitudes between the two microphone elements can be achieved.

In summary, this review of the prior art in housing design and microphone architecture for active noise canceling microphones does not teach the importance of the housing shape and dimensions as these attributes relate to the performance of the active noise canceling microphone. What would be useful is a method of designing an acoustic baffle that improves the noise canceling performance of an active noise canceling microphone.

SUMMARY

In an embodiment of the present invention, a method for designing a microphone housing improves the broadband noise canceling performance of an active noise canceling microphone system while also ensuring improved speech transmission through the system. Using this method, first and second microphone elements are selected each having a diameter “d” and a thickness “t”. The two microphone elements are aligned axially with the back surfaces in contact and secured in an axially aligned cylindrical cavity within a cylindrically shaped housing. In an alternative embodiment, a single element microphone comprising two diaphragms inside the element and having a thickness of “2t” is used in place of the two microphone elements.

The cylindrically shaped housing has an outside diameter “D,” an interior cavity of diameter of “d,” and a height “2t”. The housing is exposed to an environment comprising both speech and noise. The first microphone element is adapted to receive a signal having both voice and noise components, while the second microphone element is adapted to receive a signal that is predominantly noise. A controller processes signals from the first microphone element and the second microphone element. The near field power difference between the first microphone signal and the second microphone signal is first determined in the design process. In the event the near field power difference is more than 11 dB, the outside diameter of the microphone housing “D” is reduced. In the event the near field power difference is less than approximately 8 dB, the outside diameter of the microphone housing “D” is increased.

In another embodiment of the present invention, in the event the near field power difference is more than 11 dB, the thickness of the microphone elements “t” and, the thickness of the microphone housing “2t” is reduced.

It is therefore an aspect of the present invention to improve the performance of a dual element noise canceling microphone by employing a design method that constrains the near field power difference of the first microphone signal and the second microphone to a range from 8 dB to 11 dB.

It is another aspect of the present invention to decrease the outside dimension “D” of a cylindrically shaped housing in the event the near field power difference of the first microphone signal and the second microphone is greater than 11 dB.

It is still another aspect of the present invention to increase the outside dimension “D” of a cylindrically shaped housing in the event the near field power difference of the first microphone signal and the second microphone is less than 8 dB.

It is yet another aspect of the present invention to provide a cone shaped microphone housing with straight or curved outer surface. The cone shaped outer surface of the housing helps to increase the amplitude difference in near-field, desired speech signal between the two microphone elements used in active noise canceling microphones (described as amplitude difference in the embodiments). This shape also continues to allow excellent far field coherence between the two elements for improved active cancellation.

In another embodiment of the present invention, an active noise canceling microphone system comprises a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise. The first microphone element is directed toward a speech source and the second microphone element is simultaneously directed away from the speech source. The first and second microphone elements have a diameter “d” and a thickness “t” installed in a hollow cylindrically shaped microphone housing. The microphone housing has an outside diameter “D,” an interior cavity of diameter of “d,” and a height “2t” and is adapted to secure the first and second microphone elements aligned axially with the back surfaces in contact. In this embodiment of the present invention, the ratio of “D” over “d” is between 1 and about 2.4. Protective caps may be installed over the microphone elements. In an exemplary embodiment, “t” is about 0.15 inches. In an embodiment of the present invention, the microphone elements are electret microphones.

In yet another embodiment of the present invention, the system further comprises an active element connected to the first microphone element for receiving the first microphone signal and connected to the second microphone element for receiving the second microphone signal. In an embodiment of the present invention, an active element comprises a first adaptive filter comprising a single filter coefficient for generating a first output signal from the first and second microphone signals, a second adaptive filter comprising multiple filter coefficients for generating a second output signal from the first output signal and the second microphone signal. In this embodiment, the first output signal is used to update the first adaptive filter and the second output signal is used to update the second adaptive filter. The second output signal represents primarily speech. As will be appreciated by those skilled in the art of the present invention, other active elements maybe used to perform the functions of the active elements as described herein.

In yet another embodiment of the present invention, the first adaptive filter further comprises a first convergence parameter that is set to zero after a fixed duration following inception of control so that updating the first adaptive filter ceases to continue. The second adaptive filter further comprises a second convergence parameter and is switched to zero from a non-zero constant when the second output signal instantaneously exceeds a threshold. The first and second convergence parameters of the adaptive filters are instantaneously compared to thresholds and updated according to the first and second output signals.

DESCRIPTION OF THE DRAWINGS

A general block diagram of a noise canceling microphone system according to an embodiment of the present invention is illustrated in FIG. 1.

FIG. 3B is a graph illustrating changes in the final output power of an active noise canceling microphone system under theoretical and practical conditions.

DETAILED DESCRIPTION

Figure 1:
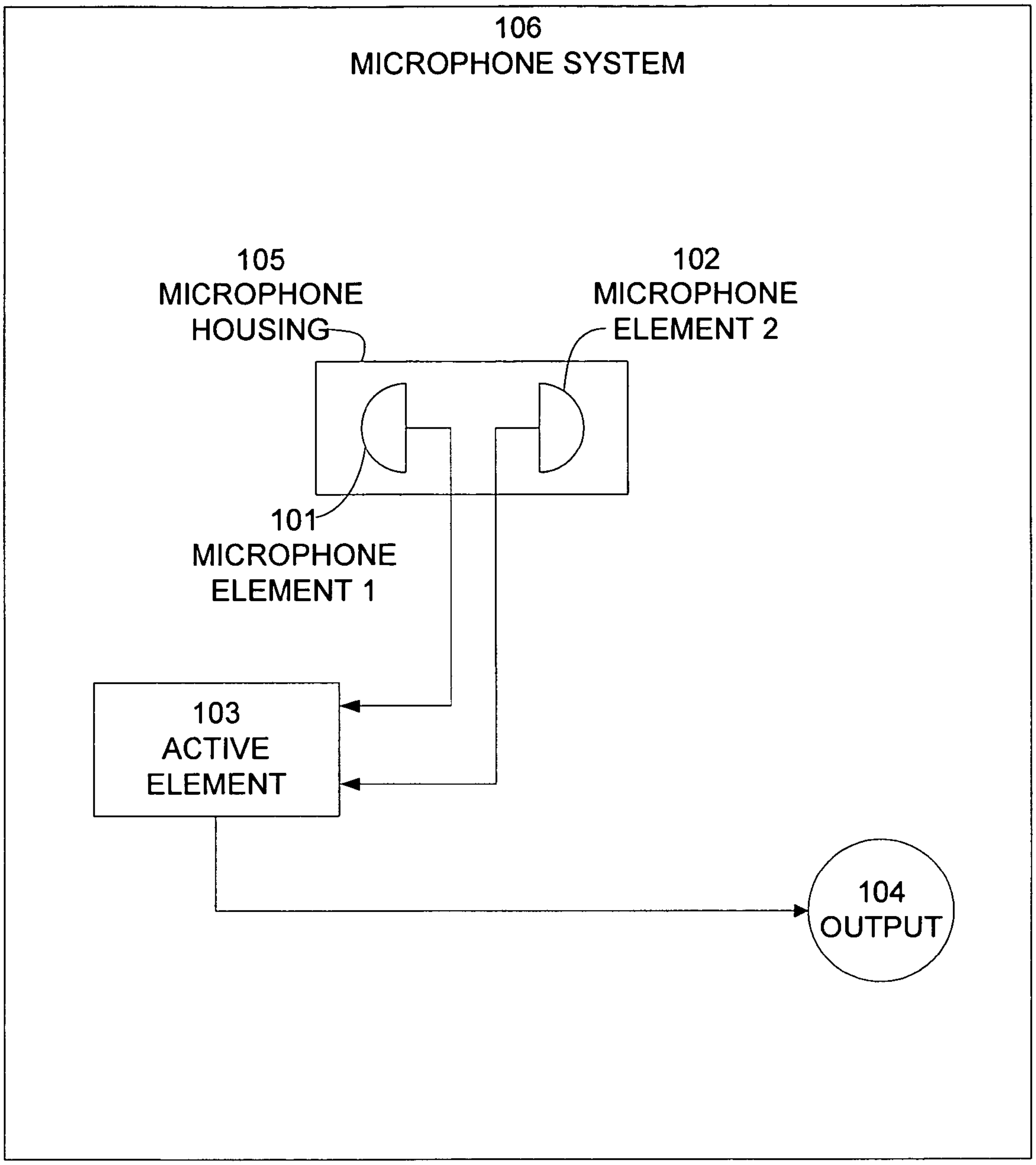

A general block diagram of a noise canceling microphone system according to an embodiment of the present invention is illustrated in FIG. 1. A first microphone element 101 and a second microphone element 102 are enclosed in a microphone housing 105 designed according to embodiments of the present invention. The outputs of first microphone element 101 and second microphone element 102 are connected to an active element 103 having an output terminal 104. The two microphone elements are arranged such that the first element 101 receives the background ambient noise and the desired signal, or the speaker's voice, while the second element 102 receives substantially only the ambient noise. When active element 103 processes the signals from first and second microphone elements (101 and 102) the ambient noise (which as a result of the baffle design of the present invention is essentially equally sensed by the two microphone elements) is cancelled out significantly, leaving a substantial amount of the desired signal at the output terminal 104.

Active element 103 comprises means for processing the signals from first microphone element 101 and second microphone element 102 so as to maximize the signal to noise ratio of the microphone system 106. In an embodiment of the present invention, active element 102 uses an LMS frequency-domain algorithm as taught in U.S. patent application No. 2002/0048377. However, the present invention is not so limited. As will be appreciated by those skilled in the art, other means, such as a time-domain algorithm, may perform the function of active element 103 without departing from the scope of the present invention.

Typically, the adaptive filtering algorithm with multiple filter taps method has better broadband (e.g., 0-4K Hz) noise canceling performance than a simple subtraction circuit approach. In general, the final output signal at the output terminal 104 of an active noise canceling microphone should minimize ambient noise as much as possible and present desired speech as high as possible. This requires that the active element 103 cancel the ambient noise sensed by the two individual microphone elements to the maximum extent while leaving the desired speech signal unaffected. These are two competing aspects affecting the active noise canceling microphone performance. The acoustic microphone housing designs described by the present invention improve the performance of this type of microphone design by effectively improving the speech discrimination and maintaining the noise measurement agreement between microphones.

It is well known that the effectiveness of the broadband feed forward active canceling process depends on the coherence function between the outputs of the microphone elements (101 and 102). The active noise canceling performance of a noise canceling microphone system may be expressed as:

$$\frac{S_a}{S_o} = 1 - \gamma^2, \tag{1}$$

where $S_a$ is the power spectral density at the output terminal 104 when the active element 103 is applied to signals from first microphone element 101 and second microphone element 102, $S_o$ is the power spectral density at the output terminal 104 when the active element 103 is by-passed and the noisy speech signal sensed by the first microphone element 101 is passed through to the output terminal 104, and $\gamma^2$ is the coherence function between the outputs of 101 and 102. Equation (1) illustrates that good noise canceling performance is directly related to the coherence function. Theoretically, if the outputs of microphone elements 101 and 102 are perfectly coherent, i.e. $\gamma^2=1$, a total cancellation of the ambient noise is achieved. The coherence function is directly related to the distance between the two microphone elements and the design of the acoustic baffle between the two microphones. The closer the two microphone elements, the better the coherence is. The more acoustically separate the microphones are, the lower the coherence becomes.

In order to prevent the desired speech from canceling itself, the magnitude of the desired speech signal received by the second microphone element 102 is minimized so as to maintain a large amplitude difference in the speech signal between 101 and 102. A means for accomplishing this objective is to provide a longer distance or an acoustic baffle between diaphragms of microphone elements 101 and 102 to increase their amplitude difference for near-field speech. However, the increase in the distance and the addition of an acoustic baffle will also degrade, to some extent, the ambient noise coherence between the two microphone elements. Since it is well known that the coherence function between the two microphone elements is directly related to distance between the diaphragms of the two microphone elements, the longer the distance, the worse the coherence. In other words, increasing the distance between the two microphone elements degrades the coherence more effectively than separating them with an acoustic baffle. Therefore when designing the housing for active noise canceling microphones, it is preferred to keep the two microphone elements as close as it is practically allowed for the coherence consideration while properly designing the acoustic baffle to minimize the near-field speech sensed by the microphone element 102.

Figure 2A:
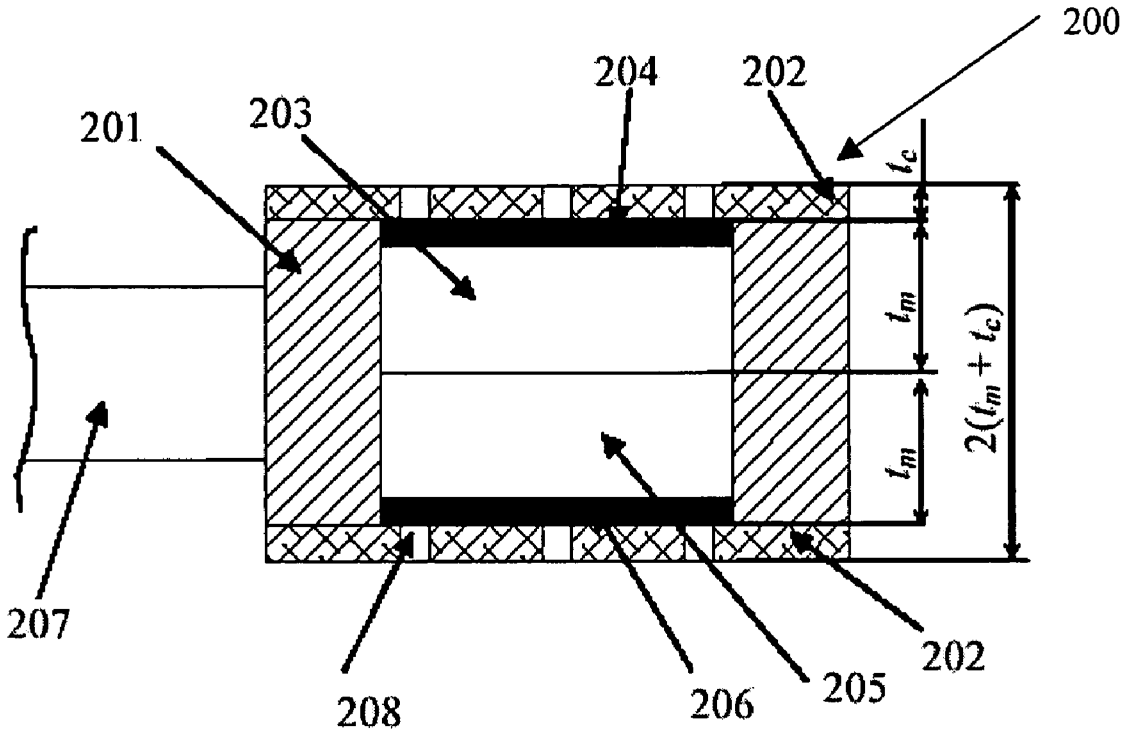
FIG. 2A illustrates a cross-sectional view of a microphone assembly according to an embodiment of the present invention.
Figure 2B:
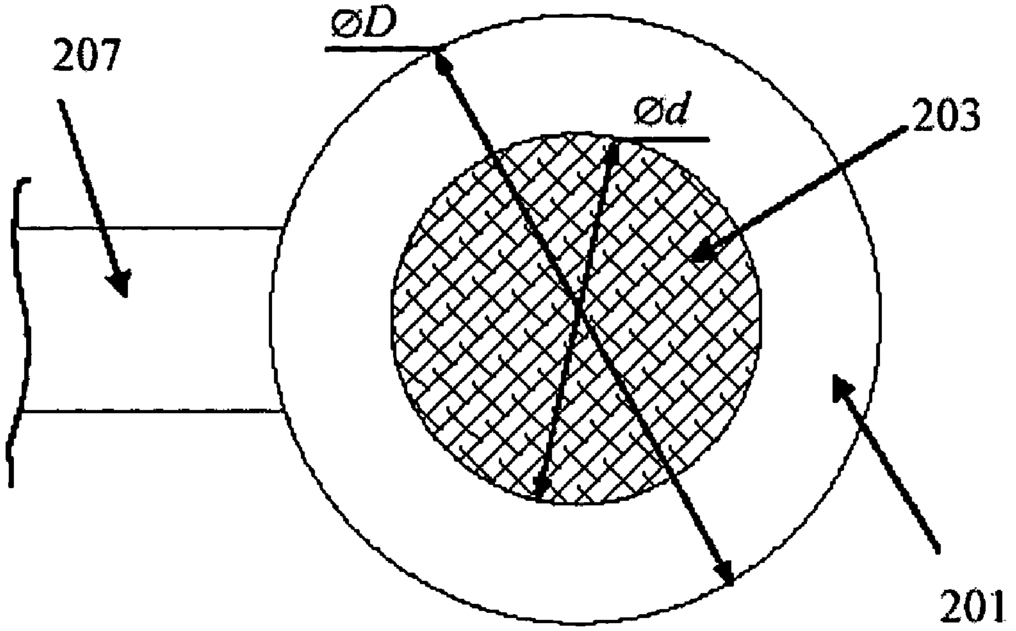
FIG. 2B illustrates a top plane view of a microphone assembly according to an embodiment of the present invention.

In an embodiment of the present invention, a design method is used to optimize the size and shape of the baffle design so as to maximize the ambient noise coherence function and enable cancellation of the ambient noise to the maximum extent as well as maintain an acoustic separation between the microphones for the near field desired speech signal. FIG. 2A illustrates a cross-sectional view of microphone assembly designed according to embodiments of the present invention. FIG. 2B illustrates a top plane view of a microphone assembly designed according to embodiments of the present invention. Referring to FIG. 2A, two microphone elements 203 and 205 each having a diameter d are placed together back-to-back inside a cylindrical microphone housing 201 with outer diameter D. The microphone element has a thickness of $t_m$ and the cylindrical housing has a height of $2t_m$. The two microphone elements are placed back-to-back to increase the amplitude difference in the near-field desired speech between the two microphone elements. In addition, this back-to-back configuration maintains the shortest distance between the diaphragms of the two microphone elements as is allowed in practice. Other configurations, such as the face-to-face or side-by-side that can result in an even closer distance between the two diaphragms will also result in a very small or no amplitude difference for near-field desired signal between the two microphone elements. Thus, those configurations are either not practical or sub-optimal for active noise canceling microphone applications.

In an embodiment of the present invention, microphone elements 203 and 205 are electret microphone elements having a small size of $t_m$, which is helpful in achieving good far field coherence as described above. It is also advantageous from a performance and implementation standpoint to use two omni-directional microphone elements since only one side of the omni-directional microphone needs to be open to the acoustic environment. This makes it possible to place two microphone elements back-to-back and helps reduce the distance between the two pressure sensitive surfaces 204 and 206. Furthermore, two omni-directional elements optimally overlap each other's directionality patterns providing a high level of coherence between the two elements. While electret microphones are utilized in this embodiment, the present invention is not so limited. As will be appreciated by those skilled in the art, other microphones may be utilized without departing from the scope of the present invention.

A cap 202 having a thickness of $t_c$ with holes 208 covers each side of the cylindrical microphone housing 201 and protects the microphone elements. The total thickness of the microphone housing assembly, $2(t_m+t_c)$, should be as small as possible to achieve good far-field coherence. This requires that once the microphone elements are selected, the cap (202) is constructed such that its thickness, $t_c$, is as small as possible but with enough structural rigidity to protect the microphone element.

The microphone housing assembly 200 is connected to an earcup or earpiece (not illustrated) through connection means 207. By way of illustration and not as a limitation, the connection means is a boom. In an embodiment of the present invention, the physical size of the connection means 207 is smaller in width than the diameter "D" of cylindrical microphone housing 201 and equal to or smaller in overall thickness $2(t_m+t_c)$, so as to not significantly impact the resulting acoustic baffle design.

A useful parameter of this acoustic baffle (housing) design is the size ratio, r, defined as $$r = \frac{D}{d}, \quad (2)$$

where "D" is the diameter of the cylindrical microphone housing and "d" is the diameter of microphone elements 203 and 205. In an embodiment of the present invention, the parameter "r" is maintained within a range between 1 and 2.4, and is preferably around 1.8. The impacts of deviation from this range will be given in the following paragraphs. Notice that the size ratio "r" is always larger than 1 since a physical wall thickness is necessary for an actual acoustic baffle and a structure is required to hold the microphone diaphragm.

FIG. 3 is a graph illustrating changes in the overall output power of an active noise canceling microphone under a fixed noise environment as a function of the amplitude difference of the desired signal, or speaker's voice, sensed by the two individual microphone elements of thickness t=0.15 inch according to an embodiment of the present invention. Referring to FIG. 1, the output power is measured at the output terminal 104. In this embodiment, the graph is obtained by a simulated experimental procedure using an active noise canceling algorithm presented in the Ser. No. 09/970,356 Application. The ambient noise signals fed into the algorithm are first recorded in a semi-reverberant noise field using two omni-directional electret microphone elements positioned in a microphone assembly similar to that illustrated in FIG. 2A. The near-field desired speech signals are then added manually (using wave file editing software and a PC) into the two recorded noise signals. In this way, it is convenient to adjust the amplitude difference in the near field desired speech between both input channels of the active noise canceling algorithm without affecting the characteristics of the ambient noise sensed by the two microphone elements.

Figure 3A:
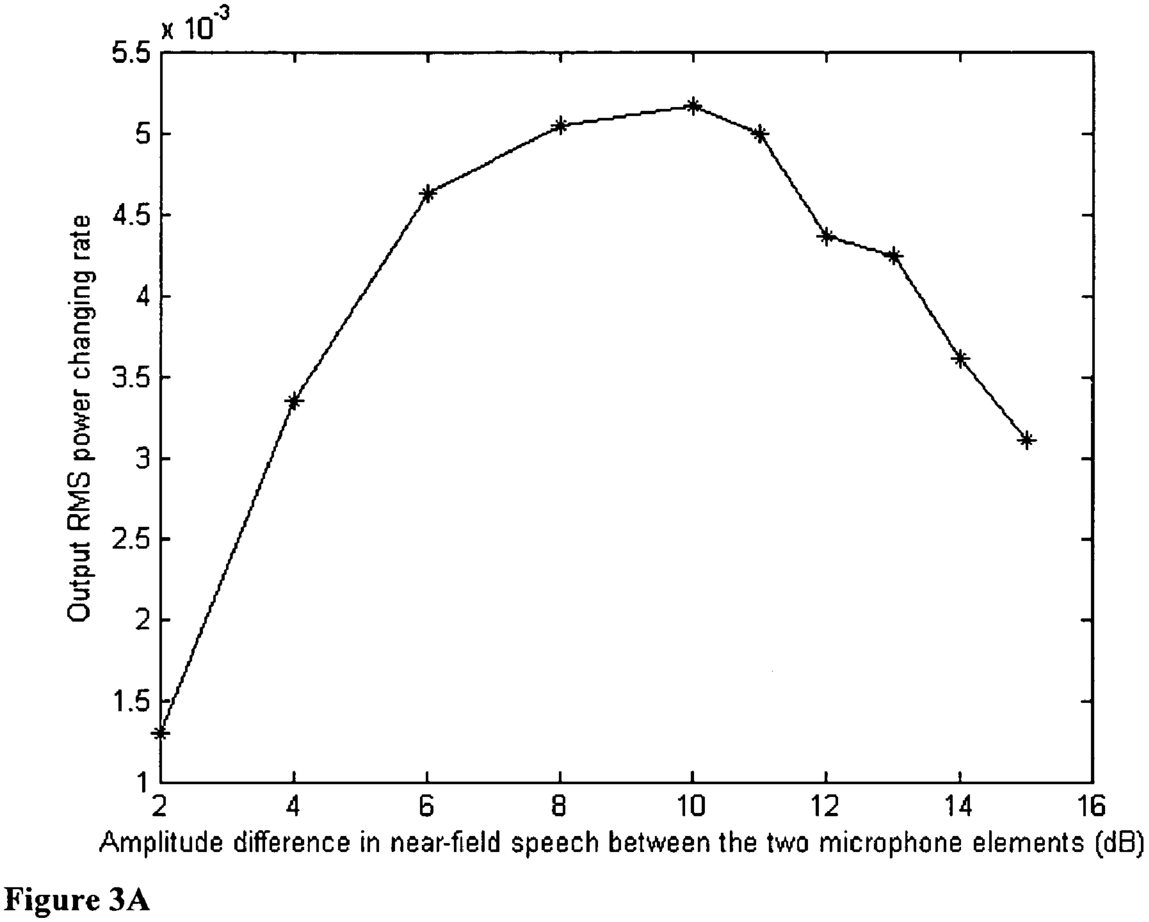
FIG. 3A is a graph illustrating changes in the final output power of an active noise canceling microphone system under a fixed noise environment as a function of the amplitude difference of the desired signal, or speaker's voice sensed by the two individual microphone elements according to an embodiment of the present invention.

In an embodiment of the present invention, the amplitude difference in the near-field speech is adjusted to keep the amplitude of the speech signal sensed by the first microphone element (101) fixed while the amplitude of the speech signal sensed by the second microphone element (102) is varied. Since the input noise remains unchanged, the output power change measured at the output terminal is essentially due to the change in the amplitude difference of the near-field speech sensed by the two microphone elements. In this simulation, a higher output power is desirable since it essentially indicates a higher speech level output or higher signal-to-noise ratio (SNR), (in effect less speech is cancelled by the active noise canceling algorithm). The horizontal axis in FIG. 3A is the near-field speech amplitude difference sensed by the two microphone elements. This amplitude difference ranges from 2 to 15 dB in the simulation. The vertical axis in FIG. 3A is the changing rate of the output power that is calculated as the amount of the output power increased (or decreased) when the near-field amplitude is increased by 1 dB. According to the definition, this changing rate is essentially the gradient of the output power. Therefore, a positive changing rate indicates an increment in the output power as a result of the increment in the near-field amplitude difference, and the higher the changing rate the higher the increment in the output power can be obtained when the near-field amplitude is increased by 1 dB. FIG. 3A also demonstrates that the output power keeps increasing when the near-field amplitude difference is increasing. However, when the desired near-field signal received by the first microphone element (101) is 8-11 dB higher than that sensed by the second microphone element (102), the output power has the highest changing rate per dB.

FIG. 3B illustrates the same method as shown in FIG. 3, collected through a simulated procedure that emulates realistic theoretical and practical results. The solid trace in FIG. 3B represents the rate of change of the output power versus the near-field power difference in the two microphone signals, when the adaptation of the controller is fixed at a value of unity. In general, the magnitude of the controller will converge to a value of unity when presented with a far field noise that arrives at the two microphone elements at essentially equal power levels. These two far field signals will then be subtracted through the controller (assumed first to be unity) yielding a minimized output power for far field noise.

Assuming an idealized scenario, that the controller only adapts to the far field noise and never adapts to the speech (as discussed in the Ser. No. 09/970,356 Application), the near field speech will experience some amount of residual cancellation due to this subtraction of the two microphone signals, because the speech will be present in both signals. The difference in power between these two signals, represented by the x-axis of FIG. 3B will vary as a function of the housing size including both thickness (t) and diameters (d and D). For the theoretically optimal case where the adaptive controller does not attempt to adapt to the speech signal, the solid trace of FIG. 3B illustrates the rate of change of output power as a function of the difference in near field microphone powers. Here we see a maximum rate of change corresponding to a 6 dB difference in close and far microphones. This indicates that for a theoretically optimal scenario, the housing should be designed to result in a 6 dB difference between the first and second microphone near-field power levels, resulting in the greatest near-field/far-field performance tradeoff.

However, in practice the adaptive filter may adapt to the near field speech and begin to cancel it during speech transients, thereby reducing the output power due solely to the speech. For a practical result where speech may be canceled by the adaptation of the controller, the adaptation transients are taken into account. For cases when the near field power difference between the two microphones is small (left side of the x-axis in FIGS. 3A and 3B), there is a significant amount of speech in the reference signal and the adaptive controller will respond and begin to cancel the speech by adjusting its gain so the filtered reference signal will appear more like the close talking signal. For higher differences in the two microphone power levels (right side of x-axis in FIGS. 3A and 3B) the adaptive controller's convergence time will prevent it from adapting fast enough to effectively cancel the speech, and the adaptive controller will appear to the near field signals largely as it appears to the far field signals.

Taking this non-linear gain change as a function of signal level into account, the rate of change of output power is altered so that its peak is shifted to between 8 and 11 dB as shown by the dotted trace in FIG. 3A. This simulated result, accounting for the adaptation of the controller and convergence rate, is nearly identical to the practical result measured for an arbitrary housing size as shown in FIG. 3A. This simulation illustrates that the optimal rate of change of output power due to near field speech is a function of the difference in the near field levels of the two microphones. For implementation with an adaptive controller such as that discussed in Ser. No. 09/970,356 Application, the optimal range for this near field power level difference is shown here to be from 8 and 11 dB. From this we can now present a method that may be used to design an optimally sized microphone housing for use with an adaptive controller.

The peak rate of change in output power represents a target design point because the maximum benefit of the output power due to the speech versus the far field cancellation has been achieved at that level. Stated differently, increasing the difference in the near field power levels normally indicates an added acoustic separation between the two microphone elements, which will necessarily decrease the coherence for far-field noise, thus reducing the benefit of the noise cancellation. Therefore, when the maximum rate of change in near field output power is reached, it represents a design point where further increases in the near field power level difference will also result in a significant decrease in ambient noise cancellation which is equally undesirable. Since this practical design point has now been established as from 8 to 11 dB, a housing may be designed for any sized microphone element. The design variables include the housing thickness, the cap thickness, and the housing diameter. For very thick microphones, a very small D will be required to achieve the desired design point, whereas for very thin microphones (t small) a larger D may be required to achieve the near field power difference of from 8 to 11 dB. The process of the design involves building a candidate housing for two microphones elements placed back to back and as close to each other as physically possible. (It should also be noted that the "two" microphone elements may alternatively be a single element with two diaphragms inside the element, effectively creating a dual diaphragm element.) The candidate housing should have a thickness equal to or not greater than the thickness of the two elements, and the caps should be as small as practical to protect the microphone elements. If the resulting near field test indicates that the power delta is too great, the housing diameter should be decreased, or the thickness should be decreased by selecting new microphone elements or redesigning the caps (which also add effective thickness). If the near field measurement results in a power difference that is too small, the diameter (D) may be increased in order to achieve the desired design point. It will generally be undesirable to move the microphones apart to achieve the near field difference because this will result in an efficient loss in far field coherence. Although an increased baffle size will also result in far-field coherence degradation, this effect is less significant than the benefit realized from near field acoustic baffling as long as the near field power difference is maintained between 8 and 11 dB.

Figure 4:
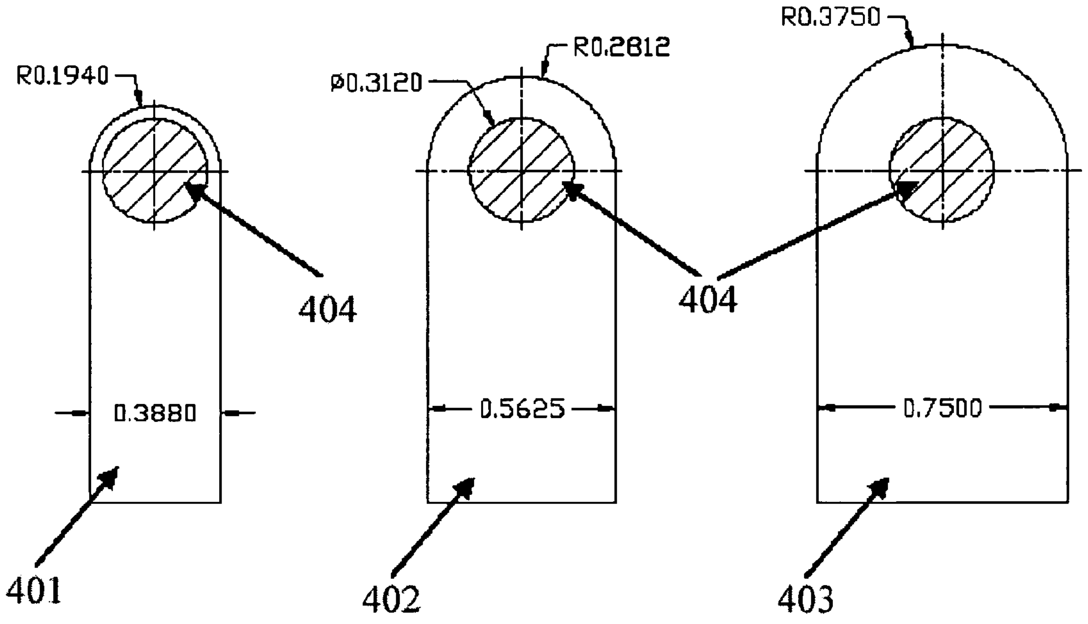
FIG. 4 illustrates three microphone assemblies with the same thickness and different ratio of the diameter of the microphone housing to the diameter of the microphone element according to an embodiment of the present invention.

To see the competing effects of the baffle (housing) size on the far-field coherence and the near-field amplitude differentiation, different baffle sizes have been tested. FIG. 4 illustrates three microphone housings 401, 402, and 403 with outer diameters of 0.388, 0.5625 and 0.75 inch, respectively. The three housings have the same thickness (2t) of 0.3 inch (reflecting a microphone element thickness of t=0.15 inch). Two electret omni-directional microphone elements (404) with a diameter of d=0.312 inch are placed back to back inside the housing. Therefore, the ratios (r) of the size of the acoustic baffle to the size of the microphone element for the three housings are $r_1$=1.24, $r_2$=1.8 and $r_3$=2.4. According to their dimensions, the three housings will be referred as the small, medium and large housing, respectively in the following text.

Figure 5:
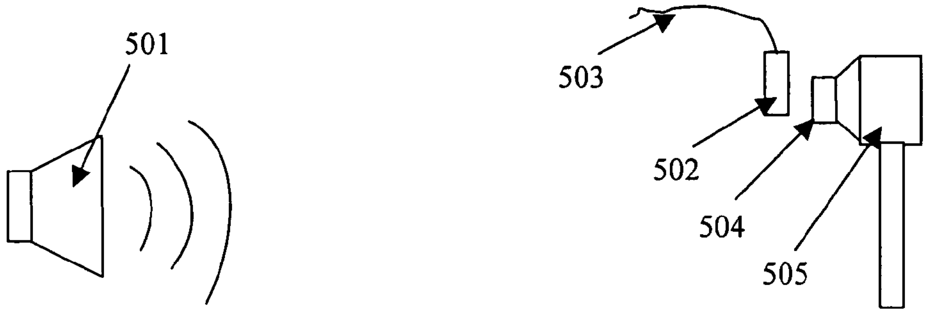
FIG. 5 illustrates a test setup for testing three microphone systems designed as shown in FIG. 4 according to an embodiment of the present invention.

FIG. 5 illustrates the experimental test setup. A loudspeaker 501 positioned in the far field is used to generate the background ambient noise. The microphone housing 502 with microphone elements is placed close to the lip-ring 504 of an artificial mouth 505. The outputs of the microphone elements are fed into the control algorithm or measurement instruments (not shown) through wire 503. Because the distance between the loudspeaker and the microphone is significantly larger than the distance between the artificial mouth and the microphone, the output from the loudspeaker is considered far-field noise to the microphone and the output from the artificial mouth is considered near-field desired signal to the microphone.

Figure 6A:
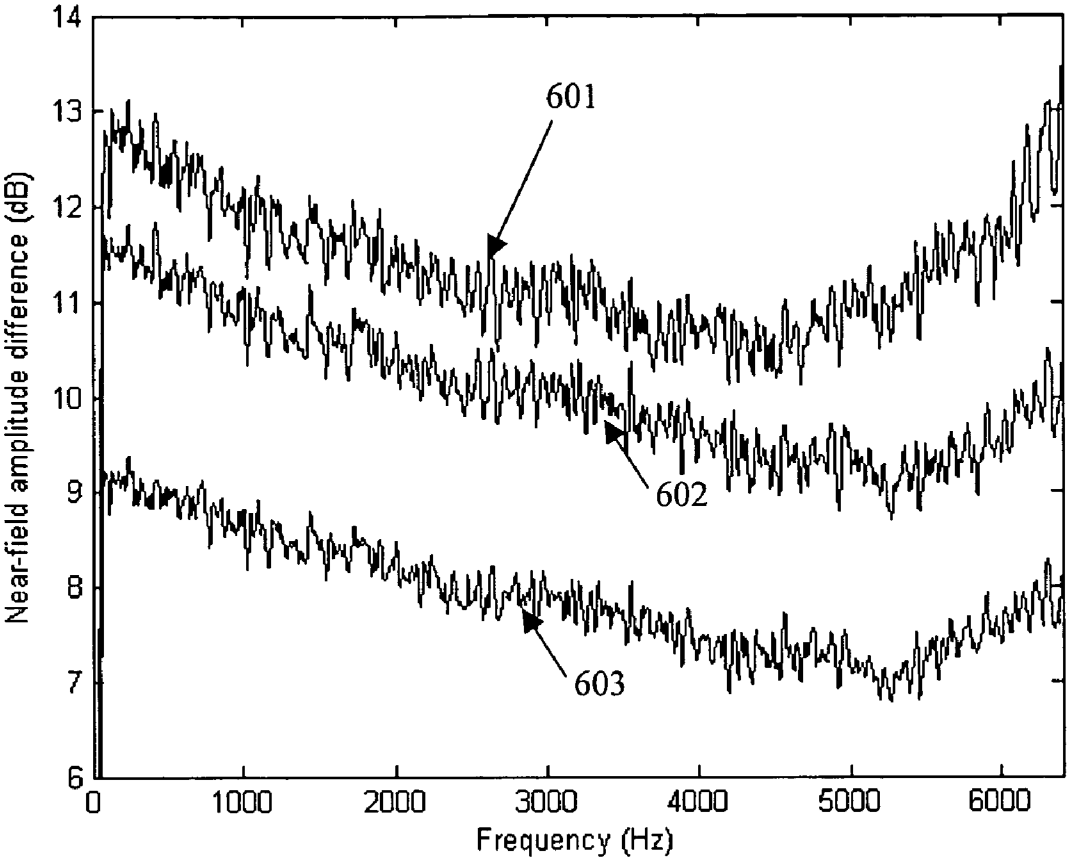
FIG. 6A is a graph illustrating an amplitude difference of the near-field, or the desired signal sensed by two microphone elements separated by the three microphone systems as shown in FIG. 4 according to an embodiment of the present invention.

FIG. 6A illustrates the test results of the near-field amplitude difference between the two microphone elements when the far-field noise is absent. In these tests, the microphone is placed about 0.05 inch away from the lip-ring. It is seen that the large baffle (housing) has the highest amplitude difference (curve 601) that is higher than 11 dB at most frequencies. The small baffle results in the smallest amplitude difference (curve 603) that is less than 9 dB at most frequencies. The amplitude difference generated by the medium baffle (curve 602) has a value between 9 and 11 dB, which is within the optimal range discussed in reference to FIGS. 3A and 3B.

Figure 6B:
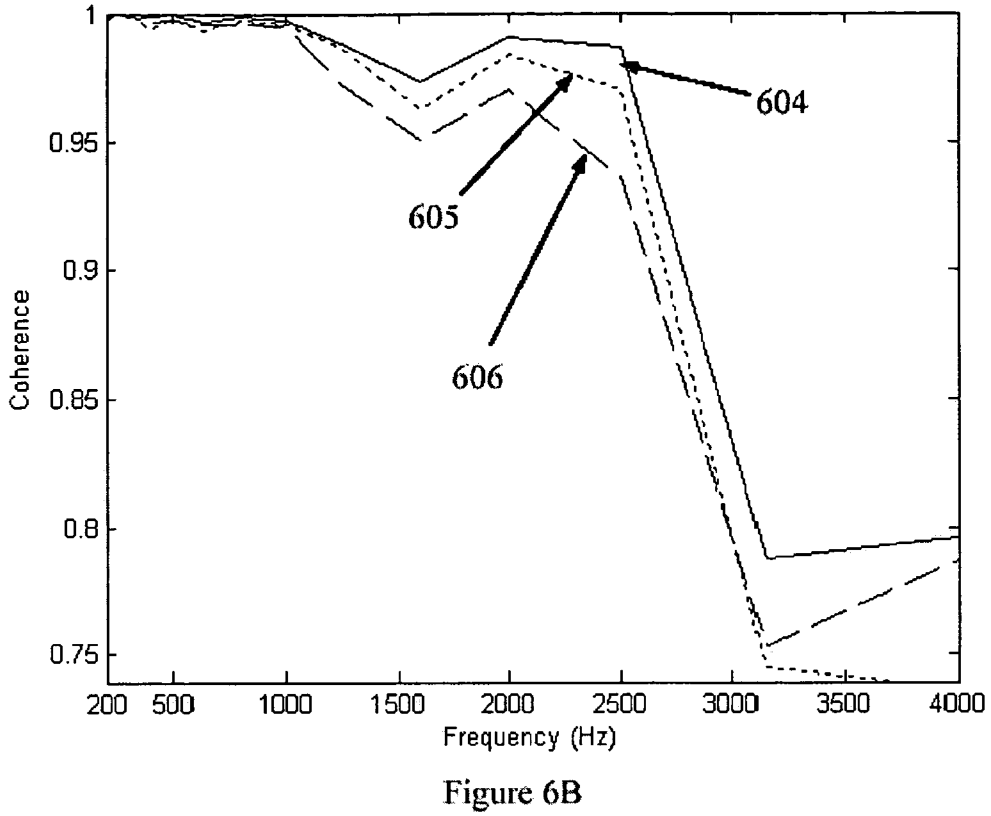
FIG. 6B is a graph of the far-field (ambient noise) coherence function between the two microphone elements separated by the three microphone systems as shown in FIG. 4 according to an embodiment of the present invention.

FIG. 6B is a graph of the far-field (ambient noise) coherence function between the two microphone elements separated by the three microphone systems as shown in FIG. 4 according to an embodiment of the present invention. Referring to FIG. 6B, the far-field noise coherence (when the near-field signal is absent) between the two microphone elements positioned inside the three housings is reversed. As it can be seen in FIG. 6B, the small baffle results in the best coherence (curve 604); the medium baffle (curve 605) results in a coherence that is worse than the small baffle but better than the large baffle (curve 606). Within the speech frequency band (200-4K Hz), the small housing results in the best average coherence of 0.9283, the medium housing results in the second best average coherence of 0.9084, and the large housing has the worst average coherence of 0.9065.

These test results indicate that the medium housing design for the microphone elements with thickness t=0.15 inch and having a size ratio (r) approximately 1.8 is a good compromise between the requirements of high far-field coherence and high near-field amplitude difference. Note that if the microphone element thickness (t) is increased while keeping d the same, the design method teaches that testing be performed to determine the best size to achieve the desired 8 to 11 dB near field power differential. This case will result in the need for a smaller housing diameter resulting in a decrease in the size ratio below 1.8.

However, if the microphone thickness (t) decreases, the microphone elements are closer together reducing the near field (voice signal) difference between the two microphone elements. In order to counteract the closeness of the two microphone elements, a new optimal size ratio is determined using the same techniques as previously outlined. In this way, the value of r is determined for a given value of t.

Figure 7A:
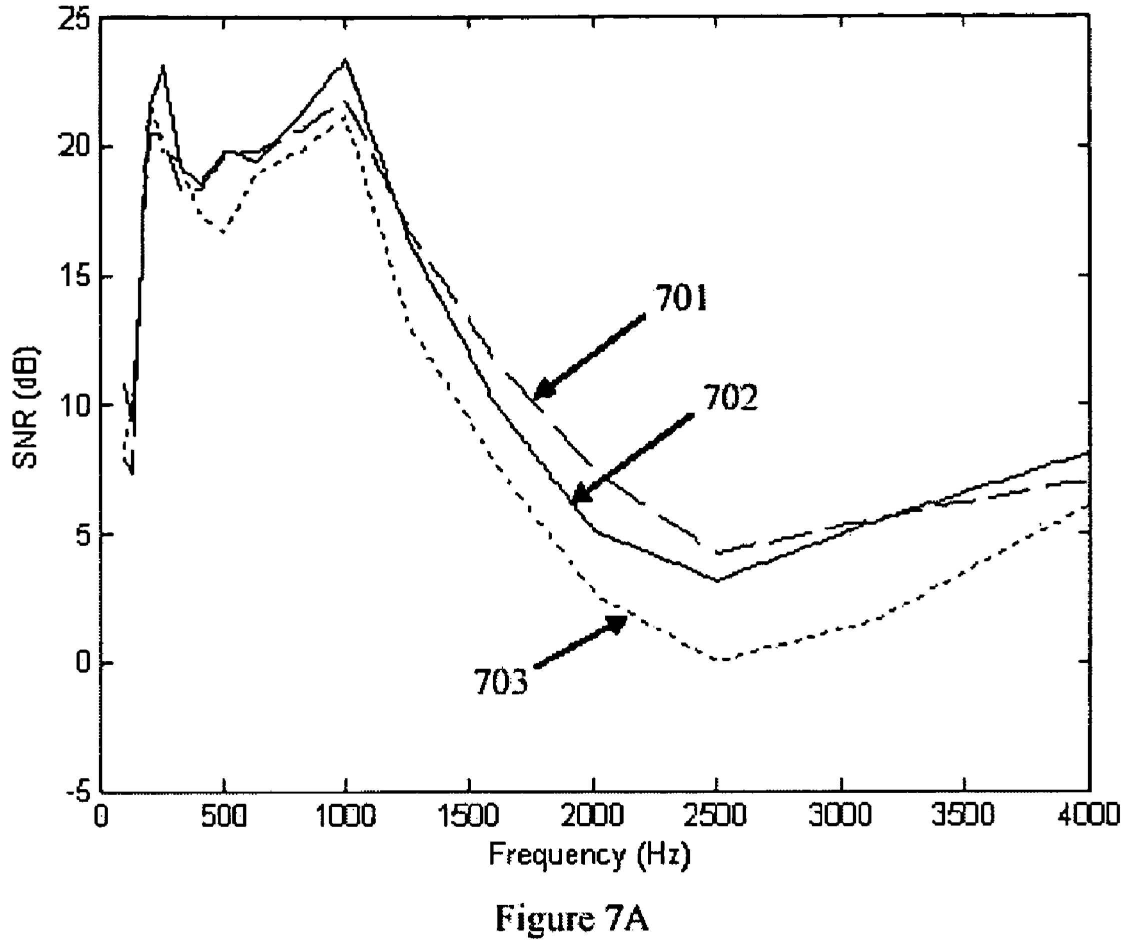
FIG. 7A is a graph illustrating a signal-to-noise ratio (SNR) as a function of frequency of the final output of an active noise canceling microphone when the microphone is placed 0.05 inch away from the near-field, or the desired signal source according to an embodiment of the present invention.

The ultimate goal of the two requirements (i.e., achieving good far field coherence and large near field power difference between the two microphone elements) mentioned above is to achieve a high signal-to-noise (SNR) ratio, i.e., the amplitude ratio of the desired near-field speech to the background ambient noise, at the output terminal of a noise canceling microphone. Therefore, the effect of microphone housing design can also be examined by measuring the output SNR. In an embodiment of the present invention, the SNR is measured using a test setup illustrated in FIG. 5. In this embodiment, the output signals of the two microphone elements inside the housing are fed into an active noise canceling algorithm presented in the Ser. No. 09/970,356 Application. The output signal amplitude and noise amplitude after the noise canceling algorithm are measured when the ambient noise is absent (the loudspeaker is off) and when the near-field voice is absent (the artificial mouth is off), respectively. They are in turn the signal amplitude and the noise amplitude of this active noise canceling microphone system in the noise field specified in the test. The SNR can then be computed. FIG. 7A illustrates the SNR as a function of frequency for the three microphone assemblies when they are placed 0.05 inch away from the lip-ring, i.e., the near-field source. It is seen that the microphone assembly with the small housing results in the best SNR (curve 701) especially above 1300 Hz. The microphone assembly with the medium housing also generates a good SNR (curve 702), which is close to the small housing. However, the microphone assembly with the large housing (curve 703) degrades the SNR significantly compared to the other two assemblies. This is due to the fact that the coherence has been degraded by the larger housing size, thus increasing the far field noise and degrading the SNR.

Figure 7B:
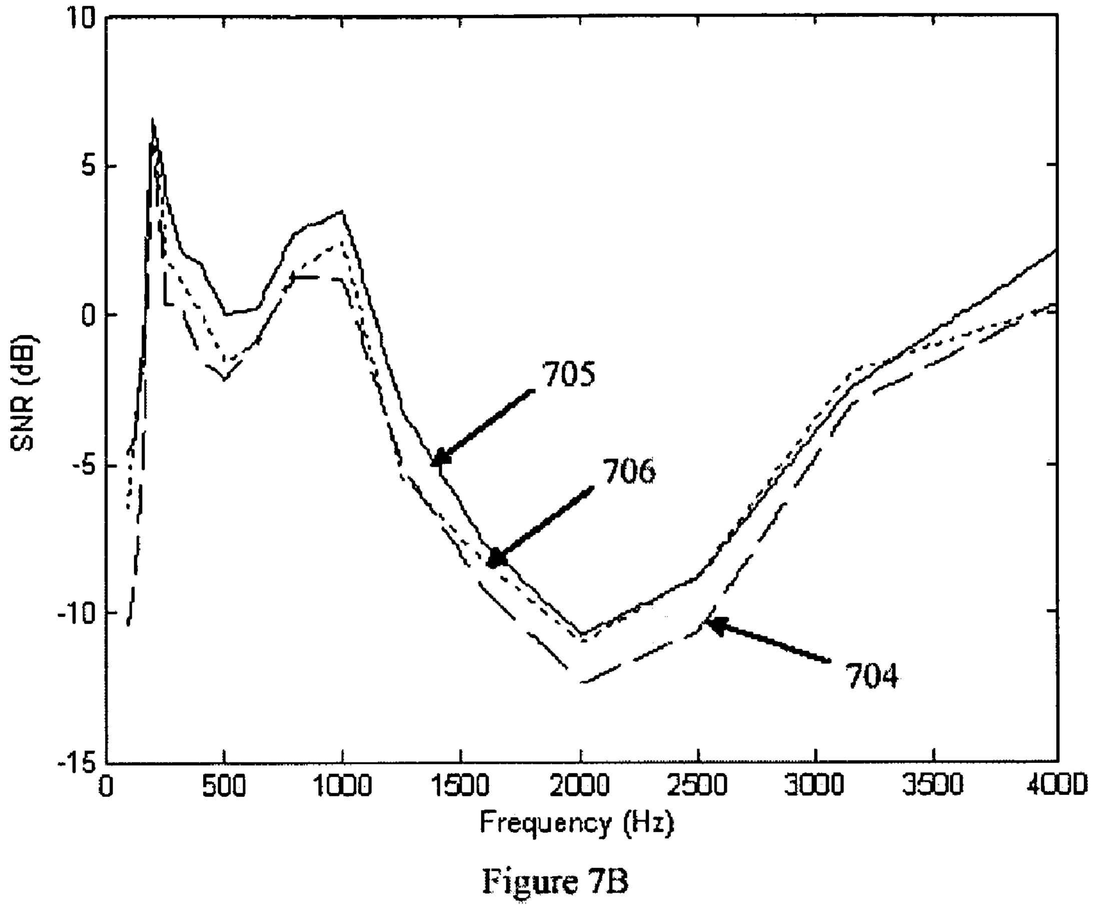
FIG. 7B is a graph illustrating a signal-to-noise ratio as a function of frequency of the final output of an active noise canceling microphone when the microphone is placed 1 inch away from the near-field, or the desired signal source according to an embodiment of the present invention.

It is well known that a noise canceling microphone performs best when it is placed as close as possible to the near-field source, or the speaker's mouth. However in practice, an operator may leave the voice microphone element up to 1 inch or even farther away from his/her mouth. FIG. 7B illustrates the SNR as a function of frequency for the three microphone assemblies when voice microphone element is placed 1 inch away from the lip-ring. Different from the observations in FIG. 7A, the microphone assembly with the small housing results in the worst SNR (curve 704). Both the microphone assemblies with the medium housing (curve 705) and large housing (curve 706) result in better SNR than the small housing. Furthermore, the microphone assembly with the medium housing whose size ratio is 1.8 results in the best SNR in this case.

FIGS. 6A, 7A and 7B teach that a microphone housing having a size ratio of around 1.8 (for t=0.15 inch) and designed to achieve a near field power difference within the range of 8 dB to 11 dB results in optimal performance of a broadband active noise canceling microphone system.

Figure 8:
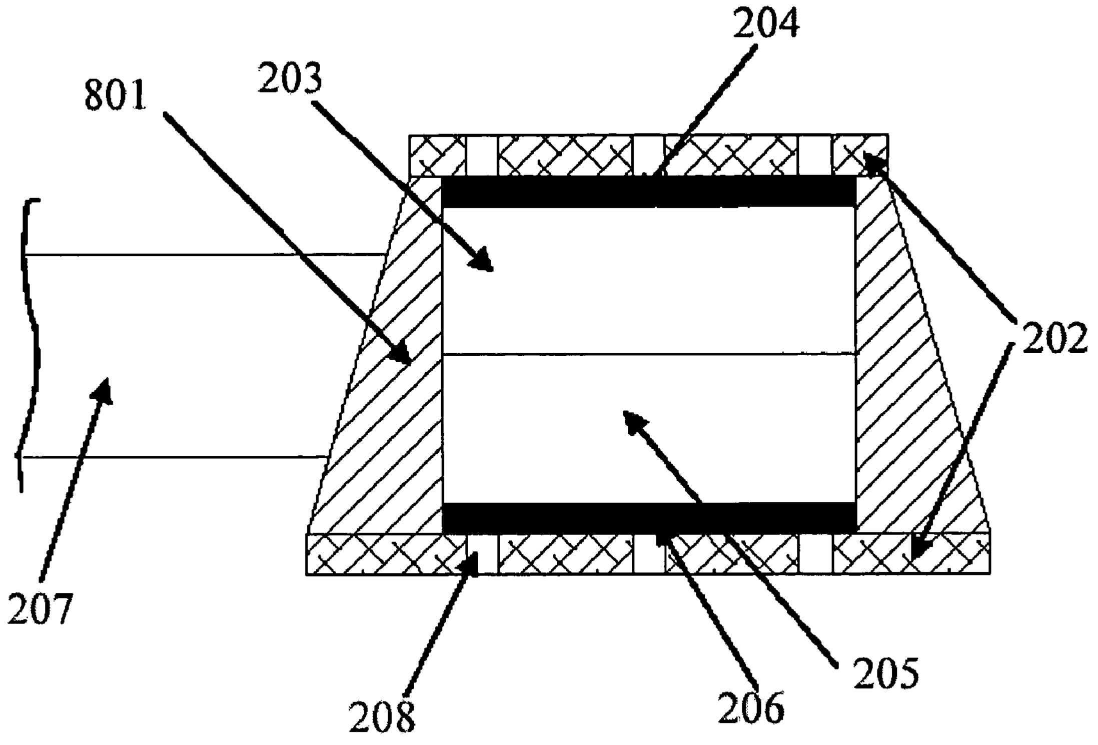
FIG. 8 illustrates a microphone assembly utilizing a microphone housing having a cone-shape outer surface according to an embodiment of the present invention.

FIG. 8 illustrates a microphone assembly utilizing a microphone housing having a cone-shape outer surface according to an embodiment of the present invention. In FIG. 8, the identical part is marked using the same numbering as in FIG. 2. The structural difference is that the microphone housing 801, has a cone-shape outer surface instead of a straight outer surface. The topside of 801, with a smaller diameter is positioned such that it faces the desired signal source, or the speaker's mouth. When the near-field speech signal arrives at the cone-shape side surface, it is deflected away from the bottom surface so that the second microphone 205 receives less near-field desired signal. Thus the amplitude difference is increased. Since the overall housing diameter of the acoustic baffle on the back side 206 of the microphone housing maintains the prescribed ratio from the above discussion, the far field noise cancellation is not significantly impacted by this alternative housing design. Because the speech reception is improved and noise rejection remains the same, the overall SNR is improved.

Figure 9:
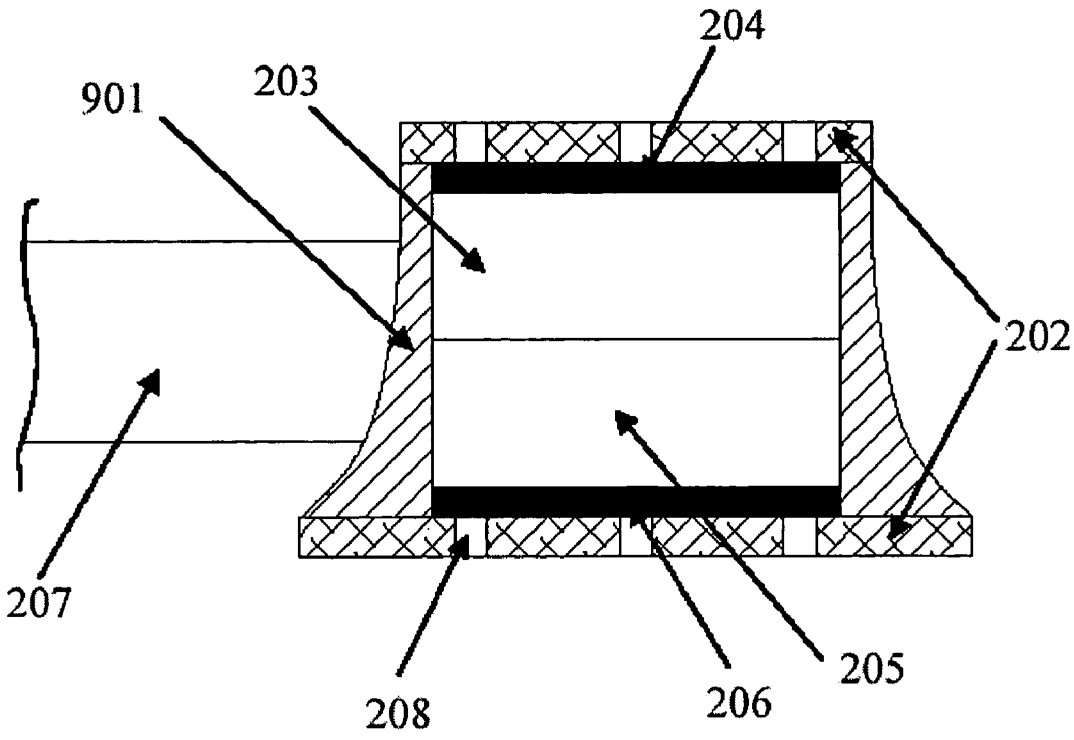
FIG. 9 illustrates a microphone assembly utilizing a microphone housing having a cone-shape curved outer surface according to an embodiment of the present invention.

FIG. 9 illustrates a microphone assembly utilizing a microphone housing having a cone-shape curved outer surface according to an embodiment of the present invention. Again, the identical part is marked using the same numbering as in FIG. 2. The structural difference is that the acoustical baffle (housing), 901, has a cone-shape curved outer surface. As described above, the topside of 901, with a smaller diameter is positioned such that it faces the desired signal source, or the speaker's mouth. When the near-field signal arrives at the cone-shaped external curved side surface, it is deflected away from the bottom surface so that the second microphone 205 receives less near-field desired signal. Thus the amplitude difference and thus signal to noise ratio is increased. Compared with the straight cylindrical side surface of 201 and the straight cone-shape side surface of 801, the curved cone-shape side surface 901 adds manufacturing complexities but is more effective to increase the near-field amplitude difference. A concave curved surface is advantageous since any point on this concave shape surface helps deflect desired near-field speech signal away from the second microphone 205. In order to maintain good far-field coherence, the size ratios of housings 801 and 901 are calculated using the larger diameter of the bottom side and should be within the optimal range suggested previously.

A method for designing a noise canceling microphone system has now been described. It will also be understood by those skilled in the art that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein the first and second microphone elements have a diameter "d" and a thickness "t"; and a hollow cylindrically shaped microphone housing having an outside diameter "D," an interior cavity of diameter of "d," and a height "2t", wherein the microphone housing is adapted to secure the first and second microphone elements aligned axially with the back surfaces in contact, and wherein the ratio of "D" over "d" is between 1 and about 2.4.

2. The system of claim 1, wherein "t" is about 0.15 inches.

3. The system of claim 1 further comprising an active element connected to the first microphone element for receiving the first microphone signal and connected to the second microphone element for receiving the second microphone signal, wherein the active element comprises:

a first adaptive filter comprising a single filter coefficient for generating a first output signal from the first and second microphone signals; and a second adaptive filter comprising multiple filter coefficients for generating a second output signal from the first output signal and the second microphone signal, wherein the first output signal is used to update the first adaptive filter and the second output signal is used to update the second adaptive filter, and wherein the second output signal represents primarily speech.

4. The system of claim 3, wherein the first adaptive filter further comprises a first convergence parameter, and wherein the first convergence parameter is set to zero after a fixed duration following inception of control so that updating the first adaptive filter ceases to continue.

5. The system of claim 3, wherein the second adaptive filter further comprises a second convergence parameter, and wherein the second convergence parameter is switched to zero from a non-zero constant when the second output signal instantaneously exceeds a threshold.

6. The system of claim 3, wherein the first and second convergence parameters of the adaptive filters are instantaneously compared to thresholds and updated according to the first and second output signals.

7. The system of claim 1, wherein the first microphone element is directed toward a speech source and the second microphone element is simultaneously directed away from the speech source.

8. The system of claim 1, wherein the first microphone element and the second microphone element are electret microphones.

9. The system of claim 1 further comprising a first protective cap covering the first microphone element, wherein the first cap comprises at least one opening, and a second protective cap covering the second microphone element, wherein the second cap comprises at least one opening.

10. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein both the first and second microphone elements have a diameter "d" and a thickness "t"; and a hollow cylindrically shaped microphone housing comprising an outside diameter "D," an interior cavity of diameter of "d," and a height "2t", wherein the microphone housing is adapted to secure the first and second microphone elements aligned axially with the back surfaces in contact, and wherein the ratio of "D" over "d" is selected to obtain a near field power difference between the first microphone signal and the second microphone signal in an acoustic environment comprising both speech and noise in the range of 8 dB to 11 dB.

11. The system of claim 10, wherein "t" is about 0.15 inches.

12. The system of claim 10 further comprising an active element connected to the first microphone element for receiving the first microphone signal and connected to the second microphone element for receiving the second microphone signal, wherein the active element comprises:

a first adaptive filter comprising a single filter coefficient, generating a first output signal from the first and second microphone signals; and a second adaptive filter comprising multiple filter coefficients, generating a second output signal from the first output signal and the second microphone signal, wherein the first output signal is used to update the first adaptive filter and the second output signal is used to update the second adaptive filter, and wherein the second output signal represents primarily speech.

13. The system of claim 12, wherein the first adaptive filter further comprises a first convergence parameter, and wherein the first convergence parameter is set to zero after a fixed duration following inception of control so that updating the first adaptive filter ceases to continue.

14. The system of claim 12, wherein the second adaptive filter further comprises a second convergence parameter, and wherein the second convergence parameter is switched to zero from a non-zero constant when the second output signal instantaneously exceeds a threshold.

15. The system of claim 12, wherein the first and second convergence parameters of the adaptive filters are instantaneously compared to thresholds and updated according to the first and second output signals.

16. The system of claim 10, wherein the first microphone element is directed toward a speech source and the second microphone element is simultaneously directed away from the speech source.

17. The system of claim 10, wherein the first microphone element and the second microphone element are electret microphones.

18. The system of claim 10 further comprising a first protective cap covering the first microphone element, wherein the first cap comprises at least one opening, and a second protective cap covering the second microphone element, wherein the second cap comprises at least one opening.

19. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein both the first and second microphone elements have a diameter “d” and a thickness “t”; and a microphone housing symmetrical about a vertical axis comprising a height “2t,” a bottom of outside diameter $D_1$ and a top of outside diameter $D_2$, wherein $D_1>D_2$, and an internal cylindrical cavity axially aligned with the top and bottom and comprising a diameter of “d,” wherein the microphone housing is adapted to secure the first microphone element in the top portion of the microphone housing and the second microphone element in the bottom portion of the microphone housing so that the first and second microphone elements are aligned axially with their back surfaces in contact, and wherein the ratio of “$D_2$” to “d” is between 1 and about 2.4

20. The system of claim 19, wherein “t” is about 0.15 inches.

21. The system of claim 19 further comprising an active element connected to the first microphone element for receiving the first microphone signal and connected to the second microphone element for receiving the second microphone signal, wherein the active element comprises:

a first adaptive filter comprising a single filter coefficient, generating a first output signal from the first and second microphone signals; and a second adaptive filter comprising multiple filter coefficients, generating a second output signal from the first output signal and the second microphone signal, wherein the first output signal is used to update the first adaptive filter and the second output signal is used to update the second adaptive filter, and wherein the second output signal represents primarily speech.

22. The system of claim 21, wherein the first adaptive filter further comprises a first convergence parameter, and wherein the first convergence parameter is set to zero after a fixed duration following inception of control so that updating the first adaptive filter ceases to continue.

23. The system of claim 21, wherein the second adaptive filter further comprises a second convergence parameter, and wherein the second convergence parameter is switched to zero from a non-zero constant when the second output signal instantaneously exceeds a threshold.

24. The system of claim 21, wherein the first and second convergence parameters of the adaptive filters are instantaneously compared to thresholds and updated according to the first and second output signals.

25. The system of claim 19, wherein the first microphone element is directed toward a speech source and the second microphone element is simultaneously directed away from the speech source.

26. The system of claim 19, wherein the first microphone element and the second microphone element are electret microphones.

27. The system of claim 19 further comprising a first protective cap covering the first microphone element, wherein the first cap comprises at least one opening, and a second protective cap covering the second microphone element, wherein the second cap comprises at least one opening.

28. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein both the first and second microphone elements have a diameter “d” and a thickness “t”; and a microphone housing symmetrical about a vertical axis having a height “2t,” a bottom of outside diameter $D_1$ and a top of outside diameter $D_2$, wherein $D_1>D_2$, and an internal cylindrical cavity axially aligned with the top and bottom and having a diameter of “d,” wherein the microphone housing is adapted to secure the first microphone element in the top portion of the microphone housing and the second microphone element in the bottom portion of the microphone housing so that the first and second microphone elements are aligned axially with their back surfaces in contact, and wherein the ratio of “$D_2$” to “d” is selected to obtain a near field power difference between the first microphone signal and the second microphone signal in an acoustic environment comprising both speech and noise in the range of 8 dB to 11 dB.

29. The system of claim 28, wherein "t" is about 0.15 inches.

30. The system of claim 28 further comprising an active element connected to the first microphone element for receiving the first microphone signal and connected to the second microphone element for receiving the second microphone signal, wherein the active element comprises:

a first adaptive filter comprising a single filter coefficient, generating a first output signal from the first and second microphone signals; and a second adaptive filter comprising multiple filter coefficients, generating a second output signal from the first output signal and the second microphone signal, wherein the first output signal is used to update the first adaptive filter and the second output signal is used to update the second adaptive filter, and wherein the second output signal represents primarily speech.

31. The system of claim 30, wherein the first adaptive filter further comprises a first convergence parameter, and wherein the first convergence parameter is set to zero after a fixed duration following inception of control so that updating the first adaptive filter ceases to continue.

32. The system of claim 30, wherein the second adaptive filter further comprises a second convergence parameter, and wherein the second convergence parameter is switched to zero from a non-zero constant when the second output signal instantaneously exceeds a threshold.

33. The system of claim 30, wherein the first and second convergence parameters of the adaptive filters are instantaneously compared to thresholds and updated according to the first and second output signals.

34. The system of claim 28, wherein the first microphone element is directed toward a speech source and the second microphone element is simultaneously directed away from the speech source.

35. The system of claim 28, wherein the first microphone element and the second microphone element are electret microphones.

36. The system of claim 28 further comprising a first protective cap covering the first microphone element, wherein the first cap comprises at least one opening, and a second protective cap covering the second microphone element, wherein the second cap comprises at least one opening.

37. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein both the first and second microphone elements have a diameter "d" and a thickness "t";

a first cap covering the first microphone element, wherein the first cap comprises at least one opening, and a second cap covering the second microphone element, wherein the second cap comprises at least one opening, and wherein the thickness of the first and second cap is no greater than required to protect the first and second sound pressure sensitive surfaces; and an external concave curved-shaped microphone housing symmetrical about a vertical axis having a height "2t," a bottom of outside diameter $D_1$ and a top of outside diameter $D_2$, wherein $D_1>D_2$, and an internal cylindrical cavity axially aligned with the top and bottom and having a diameter of "d," wherein the microphone housing is adapted to secure the first microphone element in the top portion of the microphone housing and the second microphone element in the bottom portion of the microphone housing so that the first and second microphone elements are aligned axially with their back surfaces in contact, and wherein the ratio of "$D_2$" to "d" is between 1 and about 2.4.

38. The system of claim 37, wherein "t" is about 0.15 inches.

39. The system of claim 37 further comprising an active element connected to the first microphone element for receiving the first microphone signal and connected to the second microphone element for receiving the second microphone signal, wherein the active element comprises:

a first adaptive filter comprising a single filter coefficient, generating a first output signal from the first and second microphone signals; and a second adaptive filter comprising multiple filter coefficients, generating a second output signal from the first output signal and the second microphone signal, wherein the first output signal is used to update the first adaptive filter and the second output signal is used to update the second adaptive filter, and wherein the second output signal represents primarily speech.

40. The system of claim 39, wherein the first adaptive filter further comprises a first convergence parameter, and wherein the first convergence parameter is set to zero after a fixed duration following inception of control so that updating the first adaptive filter ceases to continue.

41. The system of claim 39, wherein the second adaptive filter further comprises a second convergence parameter, and wherein the second convergence parameter is switched to zero from a non-zero constant when the second output signal instantaneously exceeds a threshold.

42. The system of claim 39, wherein the first and second convergence parameters of the adaptive filters are instantaneously compared to thresholds and updated according to the first and second output signals.

43. The system of claim 37, wherein the first microphone element is directed toward a speech source and the second microphone element is simultaneously directed away from the speech source.

44. The system of claim 37, wherein the first microphone element and the second microphone element are electret microphones.

45. The system of claim 37 further comprising a first protective cap covering the first microphone element, wherein the first cap comprises at least one opening, and a second protective cap covering the second microphone element, wherein the second cap comprises at least one opening.

46. An active noise canceling microphone system comprising:

a first microphone element comprising a first back surface and a first sound pressure sensitive surface for receiving a first microphone signal comprising speech and noise and a second microphone element comprising a second back surface and a second sound pressure sensitive surface for receiving a second microphone signal containing primarily noise, wherein both the first and second microphone elements have a diameter "d" and a thickness "t"; and an external concave curved-shaped microphone housing symmetrical about a vertical axis having a height "2t," a bottom of outside diameter $D_1$ and a top of outside diameter $D_2$, wherein $D_1>D_2$, and an internal cylindrical cavity axially aligned with the top and bottom and having a diameter of “d,” wherein the microphone housing is adapted to secure the first microphone element in the top portion of the microphone housing and the second microphone element in the bottom portion of the microphone housing so that the first and second microphone elements are aligned axially with their back surfaces in contact, and wherein the ratio of “$D_2$” to “d” is selected to obtain a near field power difference between the first microphone signal and the second microphone signal in an acoustic environment comprising both speech and noise in the range of 8 dB to 11 dB.

47. The system of claim 46, wherein “t” is about 0.15 inches.

48. The system of claim 46 further comprising an active element connected to the first microphone element for receiving the first microphone signal and connected to the second microphone element for receiving the second microphone signal, wherein the active element comprises:

a first adaptive filter comprising a single filter coefficient, generating a first output signal from the first and second microphone signals; and a second adaptive filter comprising multiple filter coefficients, generating a second output signal from the first output signal and the second microphone signal, wherein the first output signal is used to update the first adaptive filter and the second output signal is used to update the second adaptive filter, and wherein the second output signal represents primarily speech.

49. The system of claim 48, wherein the first adaptive filter further comprises a first convergence parameter, and wherein the first convergence parameter is set to zero after a fixed duration following inception of control so that updating the first adaptive filter ceases to continue.

50. The system of claim 48, wherein the second adaptive filter further comprises a second convergence parameter, and wherein the second convergence parameter is switched to zero from a non-zero constant when the second output signal instantaneously exceeds a threshold.

51. The system of claim 48, wherein the first and second convergence parameters of the adaptive filters are instantaneously compared to thresholds and updated according to the first and second output signals.

52. The system of claim 46, wherein the first microphone element is directed toward a speech source and the second microphone element is simultaneously directed away from the speech source.

53. The system of claim 46, wherein the first microphone element and the second microphone element are electret microphones.

54. The system of claim 46 further comprising a first protective cap covering the first microphone element, wherein the first cap comprises at least one opening, and a second protective cap covering the second microphone element, wherein the second cap comprises at least one opening.

* * * * *

UNITED STATES PATENT AND TRADEMARK OFFICE

CERTIFICATE OF CORRECTION

PATENT NO. : 7,245,726 B2
APPLICATION NO. : 10/928895
DATED : July 17, 2007
INVENTOR(S) : Yu Du et al.

It is certified that error appears in the above-identified patent and that said Letters Patent is hereby corrected as shown below:

Column 1, line 14, insert the following section title and paragraph before the section entitled “Background”:

--GOVERNMENT RIGHTS

This invention was made with Government support under contract N0421-03-C-0009 awarded by the Department of the Navy. The Government has certain rights in this invention. The U.S. Government has a paid-up license in this invention and the right in limited circumstances to require the patent owner to license others on reasonable terms as provided by the terms of contract N0421-03-C-0009 awarded by the Department of the Navy.--

Signed and Sealed this

Twenty-fourth Day of November, 2009

David J. Kappos
*Director of the United States Patent and Trademark Office*